(12) United States Patent
Garces et al.

(10) Patent No.: US 7,968,338 B1
(45) Date of Patent: Jun. 28, 2011

(54) **METHOD FOR CELLULAR TISSUE MULTIPLICATION FROM *JATROPHA CURCAS***

(76) Inventors: Lucia Atehortua Garces, Colombia (CO); Sandra M. Correa, Colombia (CO)

(*) Notice: Subject to any disclaimer, the term of this patent is extended or adjusted under 35 U.S.C. 154(b) by 0 days.

(21) Appl. No.: 12/829,376

(22) Filed: Jul. 1, 2010

Related U.S. Application Data

(62) Division of application No. 12/688,905, filed on Jan. 17, 2010, now Pat. No. 7,772,002.

(51) Int. Cl.
*C12N 5/02* (2006.01)
*C12N 5/04* (2006.01)

(52) U.S. Cl. ......... 435/410; 435/421; 435/431; 800/298

(58) Field of Classification Search .................. None
See application file for complete search history.

(56) References Cited

FOREIGN PATENT DOCUMENTS
WO   WO 2010/122372   * 10/2010

* cited by examiner

*Primary Examiner* — Eileen B O Hara
(74) *Attorney, Agent, or Firm* — John J Martinez; Martinez Patents PC

(57) ABSTRACT

The method of the present invention comprises: Obtaining an explant from the seeds of *Jatropha curcas*; Putting the explant derived from the seed of *Jatropha curcas* in a culture medium; Breaking the intercellular unions of the explants tissue, which generates individuals cells; Incubating for a determined time the culture medium with the generated individual cells, that were multiplied; and, Extracting oil from the cells that multiplied from the individual cells generated from the explants derived from the *Jatropha curcas* seed.

3 Claims, No Drawings

METHOD FOR CELLULAR TISSUE MULTIPLICATION FROM *JATROPHA CURCAS*

CROSS-REFERENCE TO RELATED APPLICATIONS

This application is a divisional of U.S. patent application Ser. No. 12/688,905, filed Jan. 17, 2010, now U.S. Pat. No. 7,772,002, of which the entire contents are herein incorporated by reference.

BACKGROUND OF THE INVENTION

1. Field of the Invention

The present invention is related to the multiplication of cells derived from seeds of oleaginous plants and the obtention of oils derived from the generated cells.

2. Description of Prior Art

The seeds of oleaginous plants had been identified as sources in the production of oils that could serve, among other uses, as biodiesel.

An example is the *Jatropha curcas* plant, which has a seed that contains oil. Said oil, in addition of having uses for medicine, veterinary, and soap-making, etc., is considered appropriate as a high quality biodiesel. The oil derived from the *Jatropha curcas* seed has physical-chemical and yield characteristics similar to diesel for engines (see Murali, et al., US Patent application Publication No. 2008/0194026 A1, paragraph 0008-0010).

Consequently, in the prior art, it has been described micropropagation methods with the purpose of generating *Jatropha curcas* plants derived from organs, tissues, cells, or protoplasts. (see Murali, et al., paragraphs 0014, 0017, and 0024). The generated plants could serve as source of seeds for the production of oil (see Shuyi Qiu, et al., China (CN) Patent Publication No. 11225416 A, Abstract).

Unfortunately, the possibility of oil production derived from the *Jatropha curcas* seed in big quantities for biodiesel use is limited because huge land areas are required for the harvest of plants generated by micro-propagation or conventional propagation.

The present invention provides a method for oil generation derived for *Jatropha curcas*, wherein plant growing is not required. Therefore, the method of the present invention does not need the use of land areas for oil generation derived from *Jatropha curcas*, or from other oleaginous plants.

SUMMARY OF THE INVENTION

The present invention provides a method for the production of oil derived from multiplied cells from *Jatropha curcas* seed tissue, wherein the method is applicable to other oleaginous plant seeds. Said method comprises obtaining an explant from cotyledon from a *Jatropha curcas* seed, inoculating said explant in a culture medium with enzymes which break intercellular unions, in such a way that by incubating under agitation generates individual cells which are multiplied. From the multiplied cells derived from the individual cells derived from the *Jatropha curcas* seed cotyledon tissue, the oil that could be used a biodiesel is extracted.

Specifically, the method of the present invention comprises: Obtaining an explant from the *Jatropha curcas* seed; Putting the explant derived from the *Jatropha curcas* seed in a liquid culture medium; Breaking the intercellular unions of the tissue explants derived from the *Jatropha curcas* seed in said culture, wherein the explants generate individuals cells; Incubating for a determined time the culture medium with the individual cells generated from the explants derived from the *Jatropha curcas* seed, wherein said individual cells are multiplied within the determined time; and, Extracting oil from the cells that multiplied from the individual cells generated from the explants derived from the *Jatropha curcas* seed.

In one aspect of the method of the present invention, the explant is obtained from the *Jatropha curcas* seed by a procedure which comprises: Disinfecting the *Jatropha curcas* seed with ethanol, wherein said seed is bathed with ethanol; Hydrating said disinfected *Jatropha curcas* seed with a paper wet with sterile water, wherein the paper wet with sterile water is wrapped around the *Jatropha curcas* seed; Sterilizing the hydrated *Jatropha curcas* seed with sodium hypochlorite, wherein said hydrated *Jatropha curcas* seed is bathed with sodium hypochlorite; Retiring the skin of the sterilized *Jatropha curcas* seed, wherein as a result the seed cotyledon is released from the *Jatropha curcas* seed; and, Obtaining explants from the *Jatropha curcas* seed cotyledon.

The method of the present invention could be applied to any oleaginous plant. Said method adapted to any oleaginous plant comprises:

A. Obtaining an explant from the oleaginous plant seed;
B. Putting the explant derived from the seed in a culture medium;
C. Breaking the intercellular unions of the explants tissue derived from the seed in said culture medium, wherein the explants generate individual cells;
D. Incubating for a determined time the culture medium with the individual cells generated from the explants derived from the seed, wherein said individual cells are multiplied within the determined time; and,
E. Extracting oil from the cells that multiplied from the individual cells generated from the explants derived from the seed.

In another aspect of the method of the present invention, preferably, the culture medium contains at least $NH_4NO_3$, $CaNO_3$, $CuSO_4$, $MnSO_4$, $ZnSO_4$, $H_3BO_3$. $KH_2PO_4$, $Na_2MoO_4$, EDTA, $FeSO_4$, $CaCl_2$, $CaCO_3$, $NaC_6H_7O_7$ (sodium citrate), $MgSO_4$, $K_2SO_4$, thiamine, glycine, inositol, nicotinic acid, pyridoxine, biotin, glutamine, naftalenacetic acid, zeatin, and a carbon source.

In one aspect of the culture medium of the method of the present invention, said culture medium could contain a salt selected from the group that consist of $CaNO_3$, and $KNO_3$.

In one aspect of the culture medium of the method of the present invention, said culture medium could contain a salt selected from the group that consist of $CaCl_2$, and KCl.

In another aspect of the culture medium of the method of the present invention, said culture medium could contain an hormone selected from the group that consist of indolacetic acid (IAA), naftalenacetic acid (NAA), and indolebutyric acid (IBA).

In one aspect of the culture medium of the method of the present invention, said culture medium could contain an hormone selected from the group that consist of kinetine, benziladenine (BA), Gibberelline (GA), and Zeatin.

In one aspect of the culture medium of the method of the present invention, said culture medium could contain a carbon source selected from the group that consist of saccharose (sucrose), fructose, and glucose.

In another aspect of the culture medium of the method of the present invention, cellulase, pectinase and hemicellulase are added to the culture medium, wherein the cellulase, pectinase and hemicellulase break the tissue intercellular unions of the explants derived from the *Jatropha curcas* seed in said culture medium.

In one additional aspect of the method of the present invention, the oil is extracted from the culture medium with the individual cells that were multiplied from the individual cells generated from the explants derived from the *Jatropha curcas* seed by means of a procedure that comprises: Adding an organic solvent; Sonication; Centrifugation; Extraction of the superior face; and, Evaporation and drying of the solvent.

The present invention also provides a culture medium wherein the culture medium comprises $NH_4NO_3$, $CaNO_3$, $CuSO_4$, $MnSO_4$, $ZnSO_4$, $H_3BO_3$, $KH_2PO_4$, $Na_2MoO_4$, EDTA, $FeSO_4$, $CaCl_2$, $CaCO_3$, $NaC_6H_7O_7$ (sodium citrate), $MgSO_4$, $K_2SO_4$, thiamine, glycine, inositol, nicotinic acid, pyridoxine, biotin, glutamine, naftalenacetic acid, zeatin, and a carbon source.

In one aspect of the culture medium of the present invention, said culture medium contains cellulase, pectinase and hemicellulase, wherein the cellulase, pectinase and hemicellulase break the intercellular unions of the explants tissue derived from the *Jatropha curcas* seed in said culture medium.

In one aspect of the culture medium of the present invention, said culture medium could contain a salt selected from the group that consists of $CaNO_3$, and $KNO_3$.

In one aspect of the culture medium of the present invention, said culture medium could contain a salt selected from the group that consists of $CaCl_2$, and KCl.

In one aspect of the culture medium of the present invention, said culture medium could contain a hormone selected from the group that consists of indolacetic acid (IAA), naftalenacetic acid (NAA), and indolebutyric acid (IBA).

In one aspect of the culture medium of the present invention, said culture medium could contain a hormone selected from the group that consists of kinetine, benziladenine (BA), Gibberelline (GA), and Zeatin.

In one aspect of the culture medium of the present invention said culture medium could contain a carbon source selected from the group that consists of saccharose (sucrose), fructose, and glucose.

Additional objectives and advantages of the present invention will be more evident in the detailed description of the invention and the claims.

DETAILED DESCRIPTION OF THE INVENTION

The method of the present invention comprises: Obtaining an explant from the *Jatropha curcas* seed; Putting the explant derived from the *Jatropha curcas* seed in a culture medium; Breaking the intercellular unions of the tissue explants derived from the *Jatropha curcas* seed in said culture medium, wherein the explants generate individuals cells; Incubating for a determined time the culture medium with the individual cells generated from the explants derived from the *Jatropha curcas* seed, wherein said individual cells are multiplied within the determined time; and, Extracting oil from the cells that multiplied from the individual cells generated from the explants derived from the *Jatropha curcas* seed.

In the preferred form of the method of the present invention, the preferred incubation time is at least 3 days from the moment in which the explant is put in the culture medium. In a more preferred form, the time of incubation is at least 8 days from the moment in which the explant is put in the culture medium. In a more preferred form yet the time of the incubation is at least 14 days from the moment in which the explant is put in the culture medium. The incubation is preferably performed under constant agitation at room temperature in darkness.

The incubation could also be done under illumination under a light source that emits a determined wave length, for example, infrared light, or a light source that emits the wave length that is optimal for multiplication of cells derived from a specific oleaginous plant seed.

The individual cells generated from the explants derived from the *Jatropha curcas* seed, once the intercellular unions had been broken after incubation of at least 3 days in the culture medium, can be used as a source of cells to re-inoculate in a fresh culture medium, repeating the re-inoculation repeatedly to fresh culture mediums thus enduring the multiplication of said individual cells. The preferred amount of individual cells that is re-inoculated to a fresh culture medium is from 1 to $2 \times 10^5$ cells per milliliter, and said fresh re-inoculated culture medium is incubated for a determined time until the cells reach a multiplication stationary phase.

In one aspect of the method of the present invention, the explant is obtained from the *Jatropha curcas* seed by a procedure which comprises: Disinfecting the *Jatropha curcas* seed with ethanol, wherein said seed is bathed with ethanol; Hydrating said disinfected *Jatropha curcas* seed with a paper wet with sterile water, wherein the paper wet with sterile water is wrapped around the *Jatropha curcas* seed; Sterilizing the hydrated *Jatropha curcas* seed with sodium hypochlorite, wherein said hydrated *Jatropha curcas* seed is bathed with sodium hypochlorite; Retiring the skin of the sterilized *Jatropha curcas* seed, wherein as a result the seed cotyledon is released from the *Jatropha curcas* seed; and, Obtaining explants from the *Jatropha curcas* seed cotyledon.

For purposes of the application of the present invention, the term explant refers to a portion of cotyledon from the *Jatropha curcas* seed. In the preferred form, the explant that is obtained from the *Jatropha curcas* seed cotyledon is constituted by transversally cut portions of cotyledon in laminar form from 1 to 2 mm of thickness. Explants could also be other kinds of cotyledon portions with different forms derived from the *Jatropha curcas* seed or seeds of other oleaginous plants. In the preferred form of the present invention the explant amount could be 1 to 7 grams per each 100 ml of culture medium.

The method of the present invention could be applied to any oleaginous plant. Said method adapted to any oleaginous plant comprises:

A. Obtaining an explant from the oleaginous plant seed;
B. Putting the explant derived from the seed in a culture medium;
C. Breaking the intercellular unions of the explants tissue derived from the seed in said culture medium, wherein the explants generate individual cells;
D. Incubating for a determined time the culture medium with the individual cells generated from the explants derived from the seed, wherein said individual cells are multiplied within the determined time; and,
E. Extracting oil from the cells that multiplied from the individual cells generated from the explants derived from the seed.

The term "oleaginous plant" is referred to any vegetable from which seed or fruit oil can be extracted, in some cases, edible, in other cases of industrial use and in other cases medicinal. Oleaginous plants include:

*Glycine max* (soy)
*Elaeis guineensis* (African Palm)
*Elaeis oleifera* (Noli or American oil palm)
*Arachis hypogaea* (Peanut)
*Helianthus annuus* (Sunflower)
*Zea mays* (corn)
*Linum usitatissimum* (Flax seeds)

*Brassica napus* (Colza, rape, canola or nabicol)
*Olea europaea* L. (Olive)
*Ricinus communis* (Castor oil)
*Sesamum indicum* (Sesame)
*Simmondsia chinensis* (Jojoba)
*Vernicia fordii* (Tung)
*Prunus dulcis* (Almond)
*Carthamus tinctorius* (safflower or alazor)
*Gossypium hirsutum* (cotton)
*Moringa oleifera* (drumstick tree)
*Triticum aestivum* (wheat)
and all classes of plants which seed has oil content.

In other aspect of the method of the present invention, preferably, the culture medium contains at least $NH_4NO_3$, $CaNO_3$, $CuSO_4$, $MnSO_4$, $ZnSO_4$, $H_3BO_3$. $KH_2PO_4$, $Na_2MoO_4$, EDTA, $FeSO_4$, $CaCl_2$, $CaCO_3$, $NaC_6H_7O_7$ (sodium citrate), $MgSO_4$, $K_2SO_4$, thiamine, glycine, inositol, nicotinic acid, pyridoxine, biotin, glutamine, naftalenacetic acid, zeatin, and a carbon source.

In one aspect of the culture medium of the method of the present invention, said culture medium could contain a salt selected from the group that consist of $CaNO_3$, and $KNO_3$.

In one aspect of the culture medium of the method of the present invention, said culture medium could contain a salt selected from the group that consist of $CaCl_2$, and KCl.

In one aspect of the culture medium of the method of the present invention, said culture medium could contain an hormone selected from the group that consist of indolacetic acid (IAA), naftalenacetic acid (NAA), and indolebutyric acid (IBA).

In one aspect of the culture medium of the method of the present invention, said culture medium could contain an hormone selected from the group that consist of kinetine, benziladenine (BA), Gibberelline (GA), and Zeatin.

In one aspect of the culture medium of the method of the present invention, said culture medium could contain a carbon source selected from the group that consist of saccharose (sucrose), fructose, and glucose.

In one aspect of the culture medium of the method of the present invention, cellulase, pectinase and hemicellulase are added to the culture medium, wherein the cellulase, pectinase and hemicellulase break the tissue intercellular unions of the explants derived from the *Jatropha curcas* seed in said culture medium. The intercellular unions of the explants tissue derived from the *Jatropha curcas* seed could be broken by others procedures enzymatic or non-enzymatic.

In the preferred form, the concentration ranges of the components of the culture medium of the present invention are the following:

| | |
|---|---|
| $NH_4NO_3$ | 100-500 mg/L |
| $CaNO_3$, or $KNO_3$ | 200-400 mg/L |
| $CuSO_4$ | 0.1-5 mg/L |
| $MnSO_4$ | 10-40 mg/L |
| $ZnSO_4$ | 20-50 mg/L |
| $H_3BO_3$ | 10-20 mg/L |
| $KH_2PO_4$ | 50-200 mg/L |
| $Na_2MoO_4$ | 0.1-5 mg/L |
| EDTA (ethylen-diamine-tetra-acetic acid) | 10-50 mg/L |
| $FeSO_4$ | 10-50 mg/L |
| $CaCl_2$, or KCl | 50-100 mg/L |
| $CaCO_3$ | 30-50 mg/L |
| $NaC_6H_7O_7$ (Sodium Citrate) | 0.1-10 mg/L |
| $MgSO_4$ | 50-300 mg/L |
| $K_2SO_4$ | 700-1500 mg/L |
| thiamine | 0.5-3 mg/L |
| glycine | 0.5-3 mg/L |

-continued

| | |
|---|---|
| inositol | 50-200 mg/L |
| nicotinic acid | 0.1-10 mg/L |
| pyridoxine | 0.1-10 mg/L |
| biotin | 0.1-10 mg/L |
| glutamine | 20-50 mg/L |
| IAA, or NAA, or IBA | 0.5-10 mg/L |
| zeatin, or kinetine, or BA, or GA | 0.5-10 mg/L |
| saccharose, or glucose, or fructose | 30000-100000 mg/L, and |
| hemicellulase, and pectinase, and cellulase | 3000-10000 mg/L |

In the preferred form of the method of the present invention the EDTA is disodic. The monosodic-EDTA can also be used in the method of the present invention.

In the preferred form of the method of the present invention the inositol is mio-inositol.

In the preferred form of the method of the present invention the culture medium is adjusted for a pH between 4.8 and 6.5.

In one additional aspect of the method of the present invention, the oil is extracted from the culture medium with the individual cells that were multiplied from the individual cells generated from the explants derived from the *Jatropha curcas* seed by means of a procedure that comprises: Adding an organic solvent; Sonication; Centrifugation; Extraction of the superior face; and, Evaporation and drying of the solvent.

In the case of *Jatropha curcas* or any other oleaginous plant, the oil extraction, from the cells that were multiplied from the individual cells generated from the explants derived from the seed cotyledon, is performed when the amount of cells reach an stationary phase in the culture medium. An organic solvent is added to the culture medium with the cells that were multiplied. The preferred organic solvent is hexane, thought other solvents like isopropanol or ethanol or others can be used.

The walls of the individual cells are broken when the mix of solvent, the culture medium and the individual cells are subjected to sonication, releasing the oil from the cells. The mix of solvent and culture medium that contains the broken cells and the released oil are centrifugated, which separates said mix in two phases, a superior one and an inferior one. The superior phase contains the solvent and the released oil, and the inferior phase contains said cells residues and the culture medium. The superior phase with the solvent and the oil is separated and then, the solvent of said phase is evaporated by roto-evaporation and heating, which results in the purification of oil.

The present invention also provides a culture medium wherein the culture medium comprises $NH_4NO_3$, $CaNO_3$, $CuSO_4$, $MnSO_4$, $ZnSO_4$, $H_3BO_3$. $KH_2PO_4$, $Na_2MoO_4$, EDTA, $FeSO_4$, $CaCl_2$, $CaCO_3$, $NaC_6H_7O_7$ (sodium citrate), $MgSO_4$, $K_2SO_4$, thiamine, glycine, inositol, nicotinic acid, pyridoxine, biotin, glutamine, naftalenacetic acid, zeatin, and a carbon source.

In one aspect of the culture medium of the present invention, said culture medium contains cellulase, pectinase and hemicellulase, wherein the cellulase, pectinase and hemicellulase break the inter-cellular unions of the explants tissue derived from the *Jatropha curcas* seed in said culture medium.

In one aspect of the culture medium of the method of the present invention, said culture medium could contain a salt selected from the group that consists of $CaNO_3$, and $KNO_3$.

In one aspect of the culture medium of the method of the present invention, said culture medium could contain a salt selected from the group that consists of $CaCl_2$, and KCl.

In one aspect of the culture medium of the present invention, said culture medium could contain a hormone selected from the group that consists of indolacetic acid (IAA), naftalenacetic acid (NAA), and indolebutyric acid (IBA).

In one aspect of the culture medium of the present invention, said culture medium could contain a hormone selected from the group that consists of kinetine, benziladenine (BA), Gibberelline (GA), and Zeatin.

In another aspect of the culture medium of the present invention, said culture medium could contain a carbon source selected from the group that consists of saccharose (sucrose), fructose, and glucose.

In the preferred form, the concentration ranges of the components of the culture medium of the present invention are the following:

| | |
|---|---|
| $NH_4NO_3$ | 100-500 mg/L |
| $CaNO_3$, or $KNO_3$ | 200-400 mg/L |
| $CuSO_4$ | 0.1-5 mg/L |
| $MnSO_4$ | 10-40 mg/L |
| $ZnSO_4$ | 20-50 mg/L |
| $H_3BO_3$ | 10-20 mg/L |
| $KH_2PO_4$ | 50-200 mg/L |
| $Na_2MoO_4$ | 0.1-5 mg/L |
| EDTA (ethylen-diamine-tetra-acetic acid) | 10-50 mg/L |
| $FeSO_4$ | 10-50 mg/L |
| $CaCl_2$, or KCl | 50-100 mg/L |
| $CaCO_3$ | 30-50 mg/L |
| $NaC_6H_7O_7$ (Sodium Citrate) | 0.1-10 mg/L |
| $MgSO_4$ | 50-300 mg/L |
| $K_2SO_4$ | 700-1500 mg/L |
| thiamine | 0.5-3 mg/L |
| glycine | 0.5-3 mg/L |
| inositol | 50-200 mg/L |
| nicotinic acid | 0.1-10 mg/L |
| pyridoxine | 0.1-10 mg/L |
| biotin | 0.1-10 mg/L |
| glutamine | 20-50 mg/L |
| IAA, or NAA, or IBA | 0.5-10 mg/L |
| zeatin, or kinetine, or BA, or GA | 0.5-10 mg/L |
| saccharose, or glucose, or fructose | 30000-100000 mg/L, and |
| hemicellulase, and pectinase, and cellulase | 3000-5000 mg/L |

In the preferred form of the culture medium of the present invention the EDTA is disodic. The monosodic-EDTA can also be used in the method of the present invention.

In the preferred form of the culture medium of the present invention the inositol is mio-inositol.

In the preferred form of the culture medium of the present invention is adjusted for a pH between 4.8 and 6.5.

Although the description presents preferred embodiments of the present invention, additional changes may be made in the form and disposition of the parts without deviating from the ideas and basic principles encompassed by the claims.

EXAMPLES

Ripe *Jatropha curcas* seeds, previously cleaned and washed with water and soap, were disinfected with ethanol bathes; Then, said seeds were hydrated by been wrapped around with a paper wet with sterile water; subsequently, the seeds were sterilized with 3% sodium hypochlorite bathes; Then the skin of the seed was removed with a bistoury; From the resulting cotyledon of the *Jatropha curcas* seed explants or transversal laminar portions from 1 to 2 millimeters of thickness were cut.

Between 1 to 3 grams of explants of *Jatropha curcas* seed cotyledon were placed in 100 ml of culture medium with the following composition and the following concentrations:

| | |
|---|---|
| $NH_4NO_3$ | 400 mg/L |
| $CaNO_3$ | 383 mg/L |
| $CuSO_4$ | 0.25 mg/L |
| $MnSO_4$ | 22.3 mg/L |
| $ZnSO_4$ | 8.6 mg/L |
| $H_3BO_3$ | 6.2 mg/L |
| $KH_2PO_4$ | 170 mg/L |
| $Na_2MoO_4$ | 0.25 mg/L |
| $Na_2EDTA$ (ethylen-diamine-tetra-acetic acid) | 37.3 mg/L |
| $FeSO_4$ | 27.85 mg/L |
| $CaCl_2$ | 72.5 mg/L |
| $CaCO_3$ | 20 mg/L |
| $NaC_6H_7O_7$ (Sodium Citrate) | 0.5 mg/L |
| $MgSO_4$ | 180.7 mg/L |
| $K_2SO_4$ | 990 mg/L |
| thiamine | 1 mg/L |
| glycine | 2 mg/L |
| mio-inositol | 100 mg/L |
| nicotinic acid | 0.5 mg/L |
| pyridoxine | 0.5 mg/L |
| biotin | 1 mg/L |
| glutamine | 30 mg/L |
| IAA | 2 mg/L |
| Kinetine | 1 mg/L |
| Saccharose | 50000 mg/L, and |
| pectinase, and cellulase | 5000 mg/L |

The culture medium was adjusted to a pH of 5.8 with HCL and/or NaOH 0.1 N solutions.

Said culture medium was incubated, under constant agitation, at room temperature, in the darkness for 15 days, when it was observed that explants tissue was converted to individually multiplied cells with a density of $2 \times 10^5$ individual cells per milliliter approximately.

The cells were separated from the culture medium and were re-inoculated in 100 ml of fresh culture medium of the same composition and concentrations, continuing with the incubation under constant agitation, in the darkness, for approximately 10 more days, when the cells multiplying reached a stationary state (approximately $2 \times 10^6$ individual cells per milliliter).

100 ml of hexane were added to the 100 ml of culture medium with individual cells in a density of approximately $2 \times 10^6$ individual cells per milliliter. The resulting mix was subjected to sonication for 90 minutes. Then the mix was centrifugated at 2500 rpm for 30 minutes. A superior phase and an inferior phase resulted after centrifugation. The superior phase was separated and was transferred to a recipient which was roto-evaporated at 70° C., and at 180 rpm, and then it was placed in a stove for 1 hour at 75° C. The resulting oil weighted 1.978 grams (resulting yield of 19.78 grams/L).

The oil was analyzed with the results as shown in the following table:

TABLE 1

Fatty acids estimated composition of oil sample.
Estimated composition of oil sample (gas chromatography acoplated to mass):

| FATTY ACID | RETENTION TIME (Min) | COMPOSITION %(p/p) |
|---|---|---|
| Myristic | 11.766 | 0.26 |
| Nonanodioic acid | 13.155 | 0.15 |
| Palmitic acid | 13.460 | 19.96 |
| Palmitoleic | 13.698 | 0.61 |
| Estearic | 14.994 | 8.64 |
| Oleic | 15.188 | 38.46 |
| Linoleic | 15.555 | 31.35 |
| Eicosanoic | 16.387 | 0.56 |

The composition of the obtained oil from the individual cells derived from cotyledon of the *Jatropha curcas* seed, by the method of the present invention, is similar to the reported in literature, as it is shown in the following table extract from Akintayo, E:T:, Bioresource technology 92 (2004) 307-310.

TABLE 3 of Akintayo, page 309.
Fatty acid composition (%) a of PKBS (Parkia biglobbossa) and JTC (Jatropha curcas)seeds oils

| Fatty acid | PKBS | JTC |
|---|---|---|
| Palmitic | 27.5 ± 0.5 | 19.5 ± 0.8 |
| Estearic | 10.5 ± 0.4 | 6.8 ± 0.6 |
| Oleic | 14.5 ± 0.5 | 41.3 ± 1.5 |
| Linoleic | 44.5 ± 1.5 | 31.4 ± 1.2 |
| Linolenic | 3.0 ± 0.2– | |
| Saturated | 38 | 26.3 |
| Unsaturated | 62 | 72.7 |

Values are media ± standard deviation of duplicated determinations.

The composition of oil derived from *Jatropha curcas* resulting from the method of the present invention is compared to the composition of the oil derived from *Jatropha curcas* described in literature. Therefore, the oil derived from *Jatropha curcas*, resulting from the method of the present invention, has the required characteristics for a high quality biodiesel as described in literature with respect to the oil derived from resulting from *Jatropha curcas*.

The invention claimed is:

1. A culture medium for the growth of explants and multiplication of individual cells, wherein the explants and individual cells are derived from *Jatropha curcas* seeds, wherein the culture medium comprises $NH_4NO_3$, $CaNO_3$, $CuSO_4$, $MnSO_4$, $ZnSO_4$, $H_3BO_3$, $KH_2PO_4$, $Na_2MoO_4$, EDTA, $FeSO_4$, $CaCl_2$, $CaCO_3$, $NaC_6H_7O$, (sodium citrate), $MgSO_4$, $K_3SO_4$, thiamine, glycine, inositol, nicotinic acid, pyridoxine, biotin, glutamine, naftalenacetic acid, zeatin, and a carbon source.

2. The culture medium of claim 1, wherein the culture medium contains cellulase, pectinase and hemicellulase.

3. The culture medium of claim 1, wherein the culture medium contains a carbon source selected from the group that consists of saccharose (sucrose), fructose, and glucose.

* * * * *